(12) United States Patent
Friedman et al.

(10) Patent No.: US 8,319,770 B2
(45) Date of Patent: Nov. 27, 2012

(54) METHOD AND APPARATUS FOR AUTOMATICALLY ADJUSTING USER INPUT LEFT VENTRICLE POINTS

(75) Inventors: Zvi M. Friedman, Kiriat Bialik (IL); Peter Lysyansky, Haifa (IL); Nahum Smirin, Haifa (IL)

(73) Assignee: General Electric Company, Schenectady, NY (US)

( * ) Notice: Subject to any disclaimer, the term of this patent is extended or adjusted under 35 U.S.C. 154(b) by 1169 days.

(21) Appl. No.: 12/172,097

(22) Filed: Jul. 11, 2008

(65) Prior Publication Data

US 2010/0010347 A1  Jan. 14, 2010

(51) Int. Cl.
*G06F 17/00* (2006.01)
(52) U.S. Cl. .......................... 345/418; 382/128; 382/131
(58) Field of Classification Search .......................... None
See application file for complete search history.

(56) References Cited

U.S. PATENT DOCUMENTS

| | | |
|---|---|---|
| 5,360,006 A | 11/1994 | Geiser et al. |
| 5,457,754 A | 10/1995 | Han et al. |
| 5,669,382 A | 9/1997 | Curwen et al. |
| 5,797,396 A * | 8/1998 | Geiser et al. ................... 600/407 |
| 6,346,124 B1 | 2/2002 | Geiser et al. |
| 6,447,453 B1 | 9/2002 | Roundhill et al. |
| 6,447,454 B1 * | 9/2002 | Chenal et al. ................... 600/449 |
| 6,674,879 B1 | 1/2004 | Weisman et al. |
| 6,708,055 B2 | 3/2004 | Geiser et al. |
| 6,716,175 B2 | 4/2004 | Geiser et al. |
| 6,780,152 B2 | 8/2004 | Üstüner et al. |
| 6,785,409 B1 | 8/2004 | Suri |
| 7,555,151 B2 * | 6/2009 | Comaniciu et al. ........... 382/128 |
| 2006/0058673 A1 | 3/2006 | Aase et al. |
| 2008/0267482 A1 * | 10/2008 | Abe et al. ....................... 382/131 |

* cited by examiner

*Primary Examiner* — Said Broome
*Assistant Examiner* — Janice Kau
(74) *Attorney, Agent, or Firm* — The Small Patent Law Group; Dean D. Small

(57) ABSTRACT

A method and system for optimizing user input points that identify points within an image of a left ventricle of a heart includes identifying user input points on an image. The user input points include an apical point and left and right basal points positioned proximate to an endocardium of a left ventricle. An adjusted apical point is determined based on at least an autocorrelation of points in the image proximate to the apical point. The adjusted apical point is displayed on the image.

12 Claims, 12 Drawing Sheets

METHOD AND APPARATUS FOR AUTOMATICALLY ADJUSTING USER INPUT LEFT VENTRICLE POINTS

BACKGROUND OF THE INVENTION

This invention relates generally to ultrasound imaging, and more particularly to cardiac imaging of the left ventricle.

Cardiac diagnosis is often made based on two-dimensional (2D) gray scale echo scans of the left ventricle. For example, strain computations depend on spatially smoothing the raw velocity data and limiting the computations to the myocardial territory (i.e. the heart's muscle wall). Error will generally be introduced if the myocardial borders extend to the blood pool or to the pericardial regions. The myocardial borders may be defined as the outer surface, or epicardium, and the inner surface, or endocardium, of the left ventricle. Therefore, a good estimate of the actual borders is important. The borders may be outlined manually. However, this is tedious, time consuming, and relatively subjective and user-dependent.

In order for the system to automatically calculate the myocardial borders, the user needs to identify three points in the left ventricle, the apical point and the left and right basal points. If the user places one or more of the points at an incorrect location, the results may be inconsistent and/or incorrect.

BRIEF DESCRIPTION OF THE INVENTION

In one embodiment, a method for optimizing user input points that identify points within an image of a left ventricle of a heart includes identifying user input points on an image. The user input points include an apical point and left and right basal points positioned proximate to an endocardium of a left ventricle. An adjusted apical point is determined based on at least an autocorrelation of points in the image proximate to the apical point. The adjusted apical point is displayed on the image.

In another embodiment, an ultrasound system includes a display configured to display ultrasound images that include at least one of a two chamber view, a four chamber view and an apical long axis view. A user interface is configured to receive a user input. The input defines an apical point, a left basal point and a right basal point proximate to an endocardium of a left ventricle on an ultrasound image. A processor module is configured to automatically adjust at least one of the left and right basal points based on at least the apical point. The display is further configured to display the apical point and the adjusted left and right basal points on the ultrasound image.

In yet another embodiment, a computer readable medium for optimizing user input points that identify points within an image of a left ventricle of a heart includes instructions configured to identify user input points on an image, wherein the user input points include an apical point, a left basal point and a right basal point defined proximate to an endocardium of the left ventricle. The computer readable medium further includes instructions configured to adjust at least one of the apical point and the left and right basal points based on a spatial relationship of the point to at least one of the other points. The computer readable medium further includes instructions configured to display on the image at least one of the apical point and an adjusted apical point, at least one of the left basal point and an adjusted left basal point, and at least one of the right basal point and an adjusted right basal point.

DETAILED DESCRIPTION OF THE INVENTION

Figure 1:
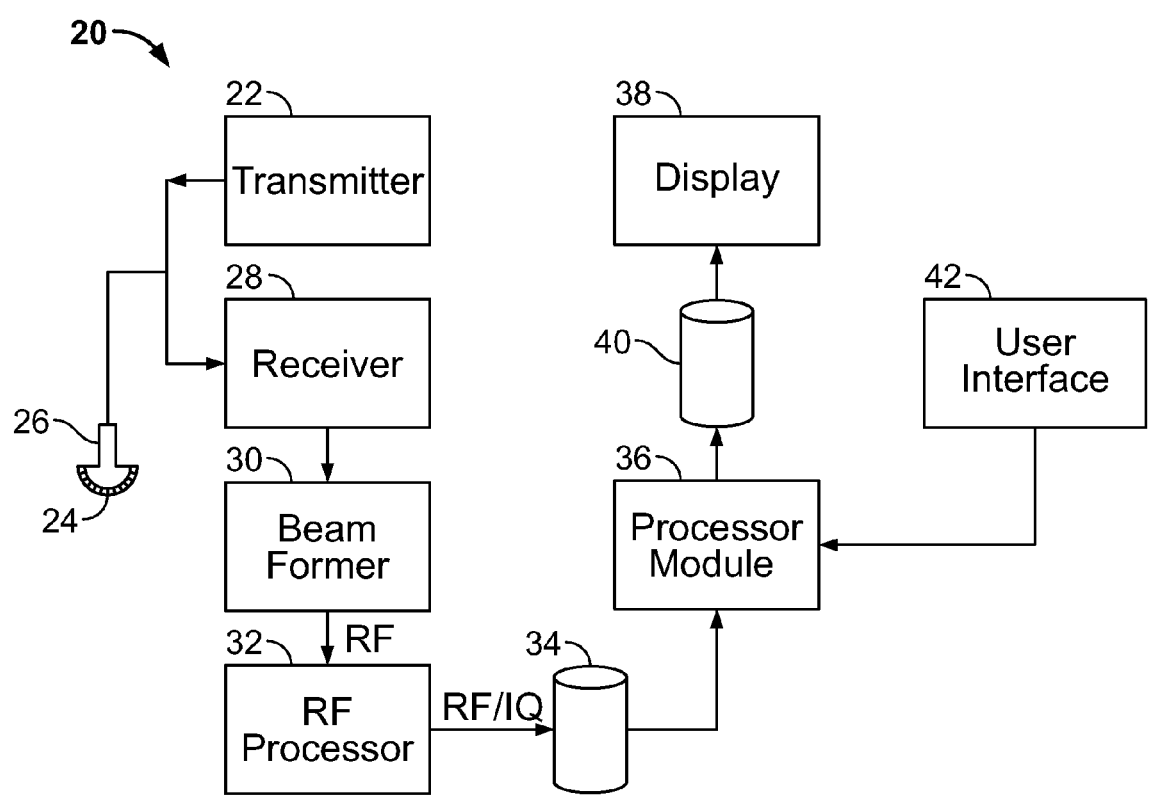
FIG. 1 illustrates a block diagram of an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates a block diagram of an ultrasound system 20. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes. The ultrasonic signals are back-scattered from structures in the body, for example, blood cells or muscular tissue, to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls some operations of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, planes from two-dimensional (2D) and/or three-dimensional (3D) ultrasound data sets stored in the memory 34 or 40. One or both of the memory 34 and the memory 40 may store 3D data sets of the ultrasound data, where such 3D data sets are accessed to present 2D and 3D images. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.).

In one embodiment, the user may need or desire to have the epicardial and endocardial borders (corresponding to the epicardium and endocardium, respectively) of the left ventricle identified, such as for strain computations. The user may position a cardiac transducer 26 to acquire one or more cardiac cycles of a patient's heart that includes at least the left ventricle. The data may be stored in the memory 40 and one or more images may be displayed on the display 38, such as an apical long axis (APLAX) view, two chamber view or four chamber view.

In one embodiment, the processor module 36 may determine a particular point in time within the cardiac cycle. The point may be related to systoli, such as being defined at the end of systoli. For example, the processor module 36 may identify a frame of data that is approximately 300 milliseconds (ms) from the start of systoli. This frame may be displayed on the display 38 for the user to identify three points thereon that are related to the left ventricle. In another embodiment, the user may select the frame. In yet another embodiment, the selected frame showing the left ventricle may be created using a different modality, such as computed tomography (CT), x-ray or MRI.

Figure 2:
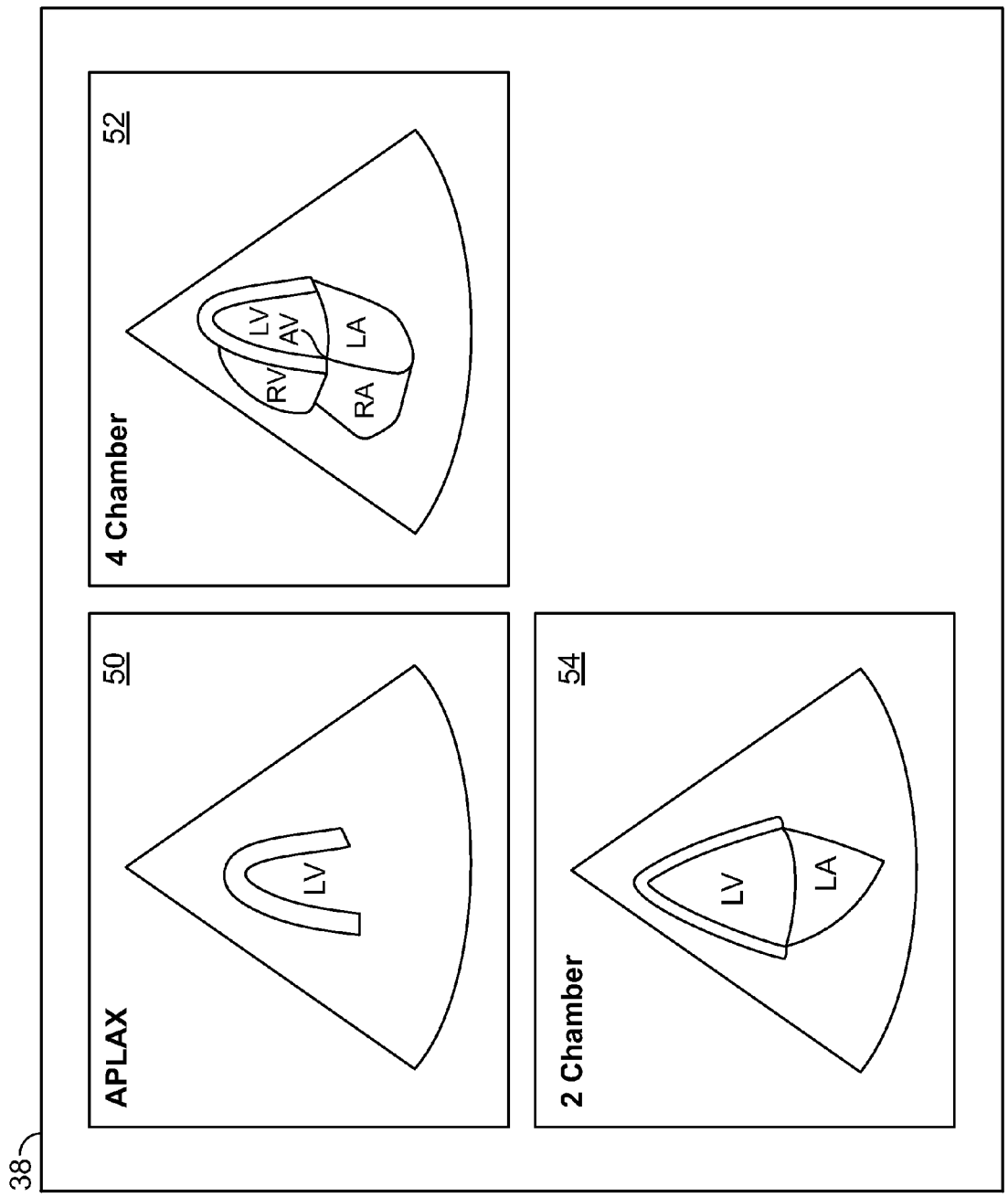
FIG. 2 illustrates examples of an APLAX view, a four chamber view and a two chamber view in accordance with an embodiment of the present invention.

FIG. 2 illustrates examples of an APLAX view 50, a four chamber view 52 and a two chamber view 54. The three points may be identified on any of the three views, however, the automatic adjustment or correction of one of the points is accomplished differently when using the APLAX view 50.

Figure 3:
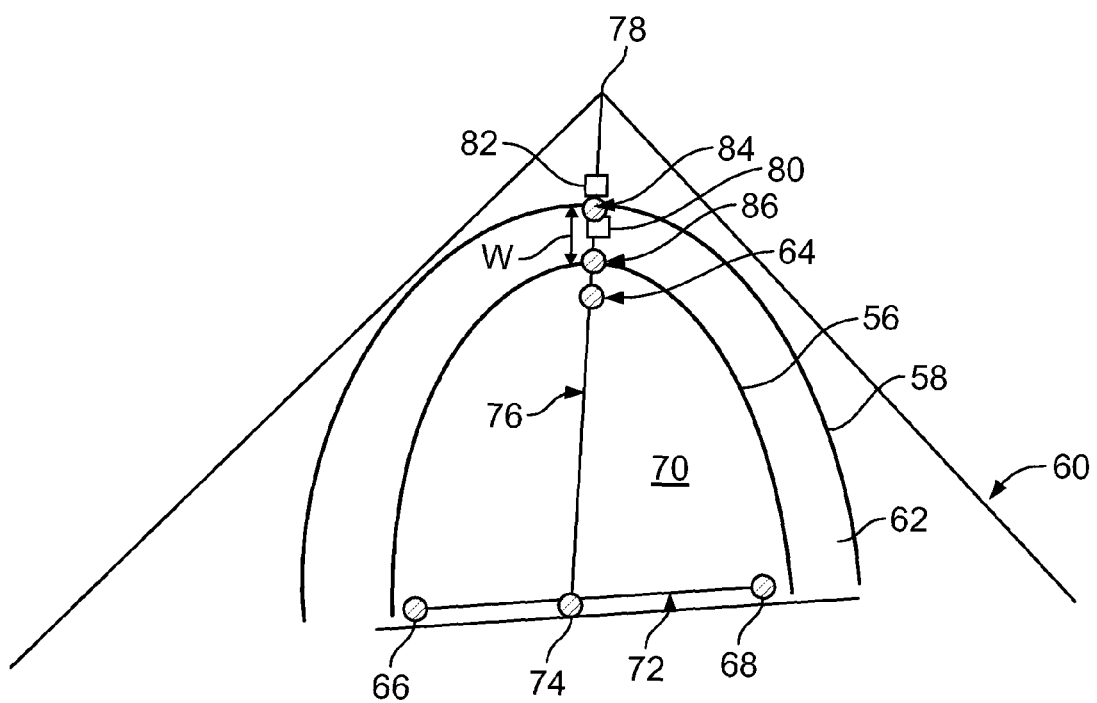
FIG. 3 illustrates a view of an ultrasound sector image of the left ventricle used to adjust a user input apical point in accordance with an embodiment of the present invention.

FIG. 3 illustrates a view of an ultrasound sector image 60 of the left ventricle 62. The user defines three points on the image 60, an apical point 64, a left basal point 66 and a right basal point 68, such as by using the user interface 42. The left and right basal points 66 and 68 are defined at or near the base of left and right inner walls (endocardium 56) of the left ventricle 62, respectively, near the mitral valve (not shown). In one embodiment, each of the points 64, 66 and 68 may be defined on the endocardium 56 of the left ventricle 62 or slightly inside blood pool 70. The processor module 36 identifies corresponding optimized points based on the three points 64, 66 and 68. In some embodiments, the processor module 36 may identify one or two corresponding optimized points based on one or two of the three points 64, 66 and 68 while not adjusting the other point(s). In yet another embodiment, the user may identify one or two of the three points 64, 66 and 68 to be optimized by the processor module 36.

Figure 4:
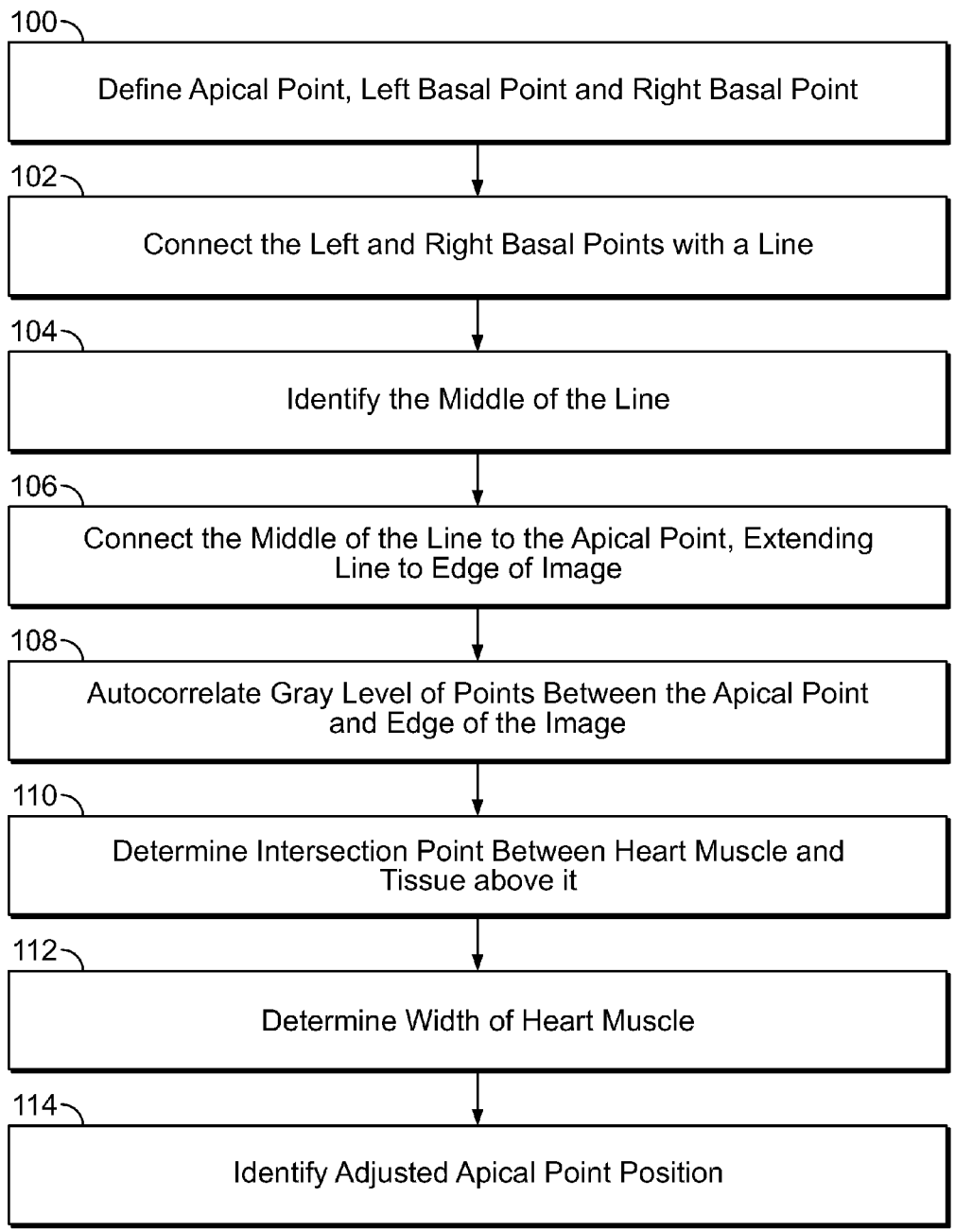
FIG. 4 illustrates a method for optimizing the apical point that a user has identified on the image of FIG. 3 in accordance with an embodiment of the present invention.

FIG. 4 illustrates a method for optimizing the apical point 64 that a user has identified on the image 60. FIGS. 3 and 4 will be discussed together. At 100, the user defines the three points on the image 60 as shown in FIG. 3, the apical point 64, the left basal point 66 and the right basal point 68. At 102, the processor module 36 connects the left and right basal points 66 and 68 with a line 72, and at 104 the processor module 36 identifies a middle point 74 along the line 72. It should be understood that other methods may be used to determine the middle point 74. At 106 the processor module 36 connects the middle point 74 to the apical point 64 with line 76, and extends the line 76 to intersect with an edge of the image 60 at intersection point 78. It is not necessary for the line 76 to intersect with the tip of the image 60 as shown in FIG. 3.

In apical views, the near zone (i.e. the imaging area near the transducer 26) is highly echogenic. However, whereas the heart muscle is in motion, contracting in systole and expanding in diastole, the region between the muscle and the transducer 26 is stationary. Therefore, the transition between the non-stationary heart muscle and the stationary tissue above the heart muscle can be determined through autocorrelation.

In another embodiment, crosscorrelation, minimum sum of absolute differences, or other methods of detecting the transition may be used.

At 108 the processor module 36 determines an autocorrelation of values, such as gray levels, temporally averaged over a period of time, such as a heart cycle, of points along line 76 that are between the apical point 64 and the edge of the image 60 or intersection point 78. For example, indicator 80 indicates a point inside the muscle of the left ventricle 62, which is a non-stationary point, and indicator 82 indicates a point above the muscle, which is a stationary point. Averaged over time, the autocorrelation of the stationary point, indicator 82, is higher than the autocorrelation of the non-stationary indicator 80. By way of example, points along the line 76 may be determined based on distance or pixels, such as by defining a point at each pixel or by separating each point by 1 millimeter (mm) or other value.

At 110 the processor module 36 determines an intersection point 84 between the heart muscle and the tissue above the heart muscle along the line 76. The intersection point 84 corresponds to a point along the line 76 that has a considerably lower autocorrelation relative to the point above the intersection point 84. For example, the intersection point 84 may be on epicardium 58. At 112 the processor module 36 determines a width w of the heart muscle, that is, the width w or distance between the endocardium 56 and the epicardium 58. The width w is assumed to be a constant throughout the horse-shoe shape of the left ventricle 62, although some variations in width w may occur from patient to patient or as a function of the position of the movement of the heart. For example, the processor module 36 may determine a size of the left ventricle 62 based on the three points 64, 66 and 68 that the user selected, and the width w may be based on the size. In another example, the user may measure a width of the septum (not shown), such as in the four chamber view 52, and that measurement may be used as the width w.

At 114 the processor module 36 adjusts the user input apical point 64 to an optimized position, adjusted apical point 86, that is located width w from the intersection point 84. Tracking algorithms may be used to track the adjusted apical point 86 in other frames throughout the heart cycle.

Figure 5:
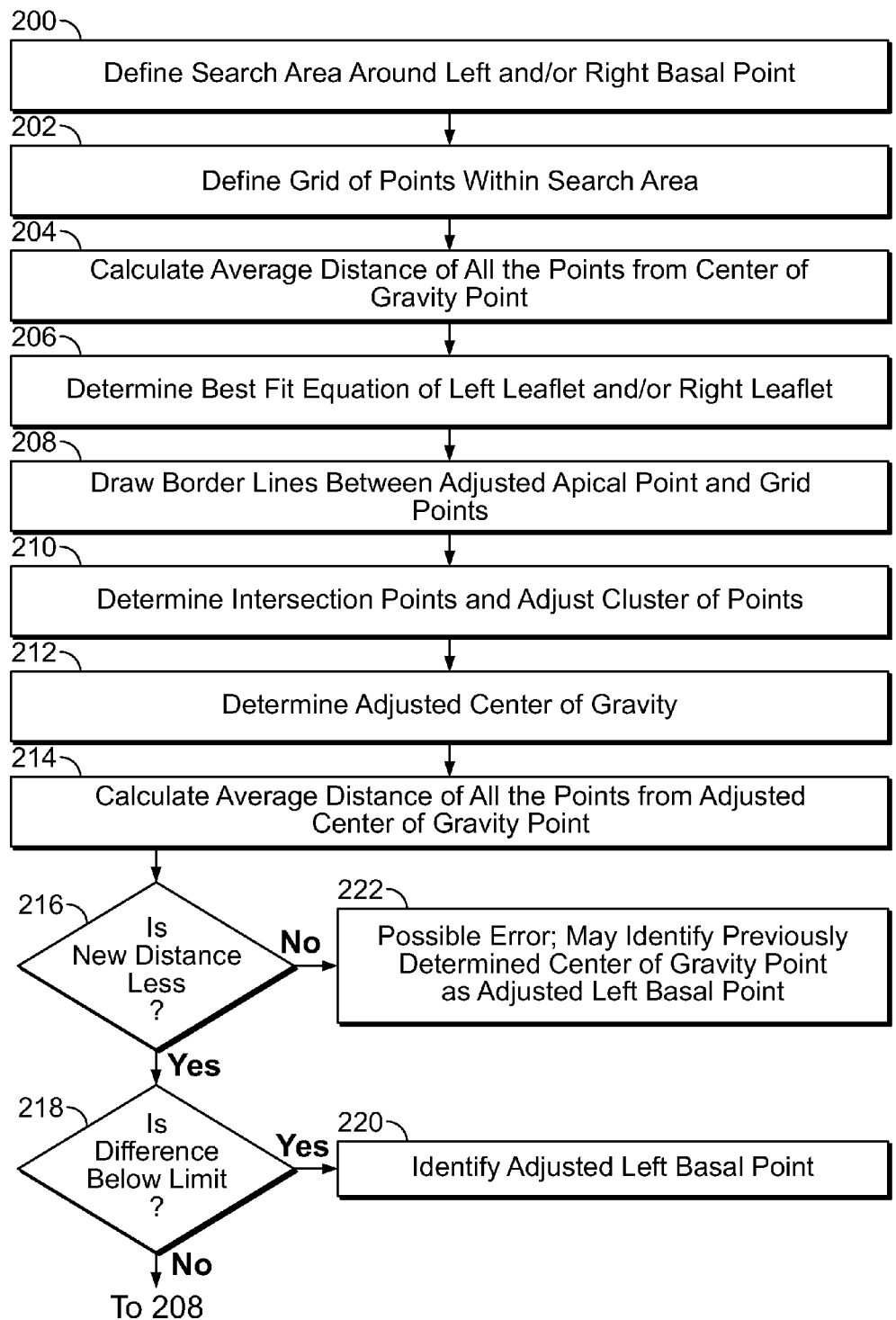
FIG. 5 illustrates a method for optimizing one or both of the left and right basal points in accordance with an embodiment of the present invention.

FIG. 5 illustrates a method for optimizing one or both of the user input left and right basal points 66 and 68. The method of FIG. 5 may be used to adjust the left and right basal points 66 and 68 in the four chamber view 52 and two chamber view 54, as well as the left basal point 66 in the APLAX view 50. However, a different method is used to adjust the right basal point 68 in the APLAX view 50, and will be discussed further below.

Figure 6:
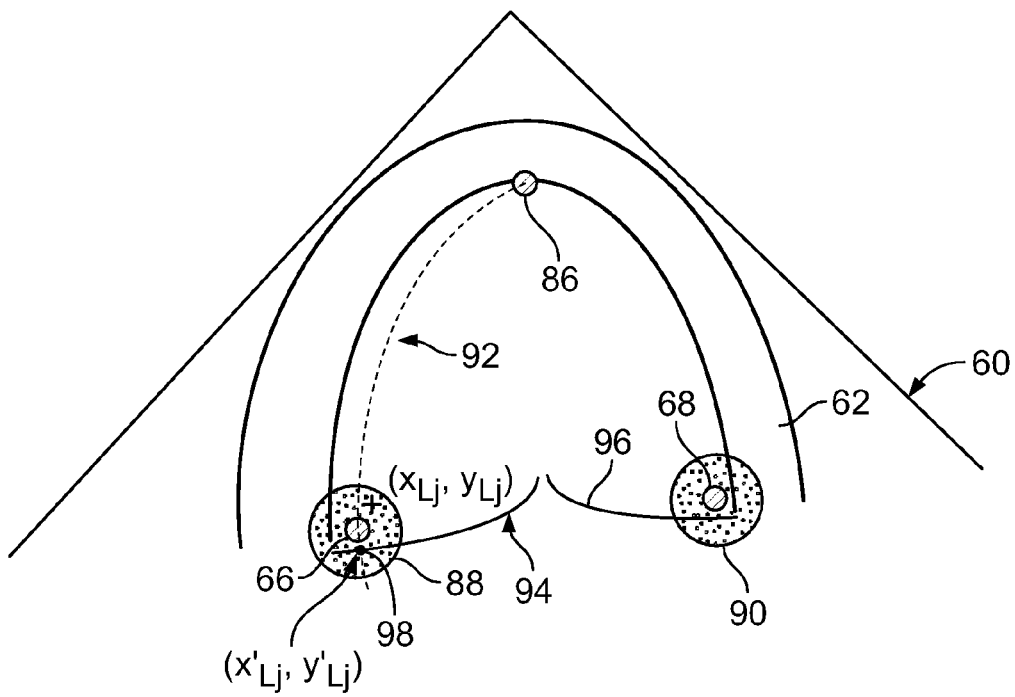
FIG. 6 illustrates a sector image and the adjustment of the left and/or right basal points in accordance with an embodiment of the present invention.

FIG. 6 illustrates the sector image 60 and the adjustment of the left basal point 66. It should be understood that the adjustment of the right basal point 68 in the four chamber view 52 and the two chamber view 54 may be accomplished in the same manner. FIGS. 5 and 6 will be discussed together.

Returning to FIG. 5, the method uses either the user input apical point 64 or the adjusted apical point 86 when adjusting the left and/or right basal points 66 and 68. For example, if the user input apical point 64 has been adjusted, the method uses the adjusted apical point 86. In another embodiment, the user may not wish to have the user input apical point 64 adjusted, and the method uses the user input apical point 64. The following discussion utilizes the adjusted apical point 86. At 200 the processor module 36 defines a circular search area 88 with the left basal point 66 as the center of the search area 88. In some embodiments, the search area 88 may be different shapes, such as a square, and different sizes as required or desired. If the image 60 is a four chamber view 52 or two chamber view 54, the processor module 36 may define a second circular search area 90 with the right basal point 68 as the center of the search area 90. The processor module 36 may determine optimized locations for the left and right basal points 66 and 68 concurrently, however, the below discussion is primarily limited to the adjustment of the left basal point 66.

At 202 the processor module 36 defines a plurality of points within the search area 88. For example, starting from the left basal point 66, a grid of points $[(x_{L,j}, y_{L,j}), j=1, \ldots, N]$ may be generated within the search area 88. The grid is initially defined such that a center of gravity point of the grid is at the user input left basal point 66. By way of example only, the number of points within the plurality of points may be 25, 27 or 36, but it should be understood that any number of points may be used. The center of gravity point may also be referred to herein as $(x_{BL,0}, y_{BL,0})$. In one embodiment, the points in the plurality of points may be formed equidistant or at regular intervals with respect to each other, such as in a grid pattern, while in another embodiment, the points in the grid may be irregularly spaced with respect to each other. At 204, the processor module 36 calculates an average distance $d_{average}$ of all of the points in the grid from the center of gravity point, which in the illustrated case is the left basal point 66.

At 206 the processor module 36 determines an equation that best fits the left leaflet (not shown) of the mitral valve. The best fit equation is illustrated as left leaflet shape 94. For example, a quadratic equation, second order polynomial, parabola, straight line, third order function and the like may be fit to bright (echogenic) portions of the left leaflet, defining the shape of the left leaflet. With respect to the right basal point 68, the processor module 36 finds an equation that best fits the right leaflet (not shown), which is illustrated as right leaflet shape 96.

At 208 the processor module 36 calculates a plurality of border lines between the adjusted apical point 86 and each of the plurality of points $[(x_{L,j}, y_{L,j}), j=1, \ldots, N]$. A single border line 92 is illustrated, drawn from the adjusted apical point 86 and extending through the left basal point 66. The border line 92 is a smoothly shaped line that is fitted to both of the points 66 and 86 and that describes a border of the endocardium 56. In FIG. 6, the border line 92 has an elliptical shape but is not so limited. In one embodiment, the portion of the border line 92 between the two points 66 and 86 may be adjusted and/or reshaped based on edges that may be detected close to the border line 92.

At 210 the processor module 36 determines intersection points between the left leaflet shape 94 and the border lines 92 extending from the adjusted apical point 86 through the points in the grid. Continuing the example above, an intersection point 98 $(x'_{L,j}, y'_{L,j})$ is indicated at the point of intersection between border line 92 and left leaflet shape 94. The current plurality or grid of points is adjusted to generate a new plurality or cluster of points $[(x'_{L,j}, y'_{L,j}), j=1, \ldots, N]$ by moving each point in the grid to a respective intersection point 98. The adjusted points in the new cluster may no longer be uniformly distributed or contained within the search area 88.

At 212 the processor module 36 determines a new or adjusted center of gravity point $(x'_{BL,0}, y'_{BL,0})$ corresponding to the adjusted cluster of points. At 214 the processor module 36 calculates the distance from each of the points $[(x'_{L,j}, y'_{L,j}), j=1, \ldots, N]$ to the new center of gravity point $(x'_{BL,0}, y'_{BL,0})$ and determines an average distance $d'_{average}$. The iteration results in a shift in the center of gravity from $(x_{BL,0}, y_{BL,0})$ to $(x'_{BL,0}, y'_{BL,0})$, with a new width or distance of $d'_{average}$.

At 216 the processor module 36 determines whether the new distance $d'_{average}$ is less than the previous distance $d_{aver}$- age. If the new average distance is not less, at 222 the processor module 36 may indicate that the process is not converging or that an error has occurred. In some embodiments, a previously determined center of gravity point may be identified as the adjusted or optimized left basal point. If the new average distance is less at 216, the process is converging, and at 218 the processor module 36 determines whether the difference between the new and previous distances is below a predetermined limit or threshold. If the difference is not below a predetermined limit, the process returns to 208 to accomplish another iteration to determine a new center of gravity point and a new average distance. For example, the predetermined limit may be defined in mm or pixels, such as 1 pixel, 1 mm, or a value less than 1 mm.

Figure 7:
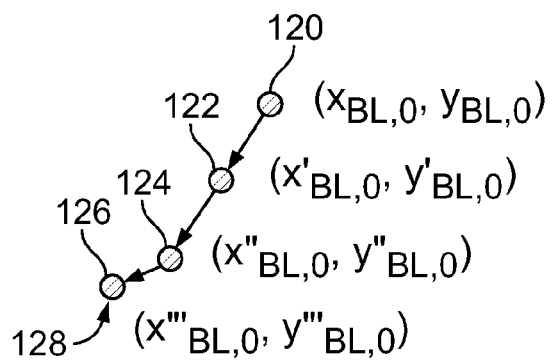
FIG. 7 illustrates a schematic representation of the convergence process of successive centers of gravity corresponding to the left basal point in accordance with an embodiment of the present invention.

FIG. 7 illustrates a schematic representation of the convergence process of successive centers of gravity corresponding to the left basal point 66. Point 120 is the user input left basal point 66, referred to as $(x_{BL,0}, y_{BL,0})$. Point 122 is the center of gravity point $(x'_{BL,0}, y'_{BL,0})$ after one iteration, point 124 indicates the center of gravity point $(x''_{BL,0}, y''_{BL,0})$ after two iterations, and point 126 indicates the center of gravity point $(x'''_{BL,0}, y'''_{BL,0})$ after three iterations. By way of example only, the distance between the center of gravity points may be decreasing by an order of magnitude with each iteration.

Returning to 218 of FIG. 5, if the difference between consecutive centers of gravity is below the predetermined limit, at 220 the processor module 36 identifies the last determined center of gravity point as the adjusted or optimized left basal point. In the example of FIG. 7, the point 126 may also be referred to as the adjusted left basal point 128. When optimized, the adjusted left basal point 128 may define the point where the left leaflet of the mitral valve intersects with the endocardium 56.

As discussed previously, when the image 60 is the four chamber view 52 or two chamber view 54, the user input right basal point 68 may be adjusted and/or optimized in the same manner as discussed above with respect to the user input left basal point 66.

Figure 8:
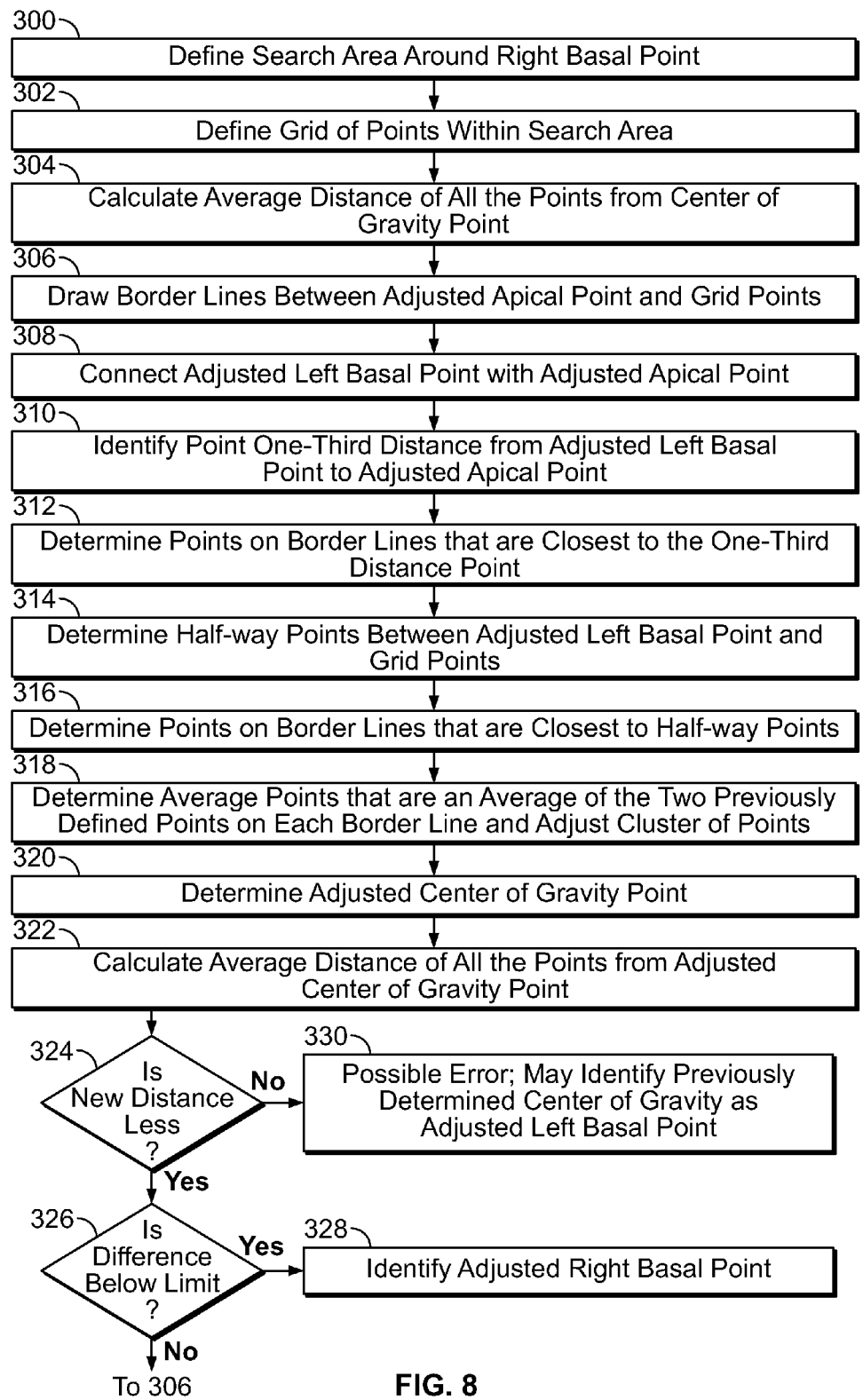
FIG. 8 illustrates a method for optimizing the right basal point in the APLAX view in accordance with an embodiment of the present invention.
Figure 9:
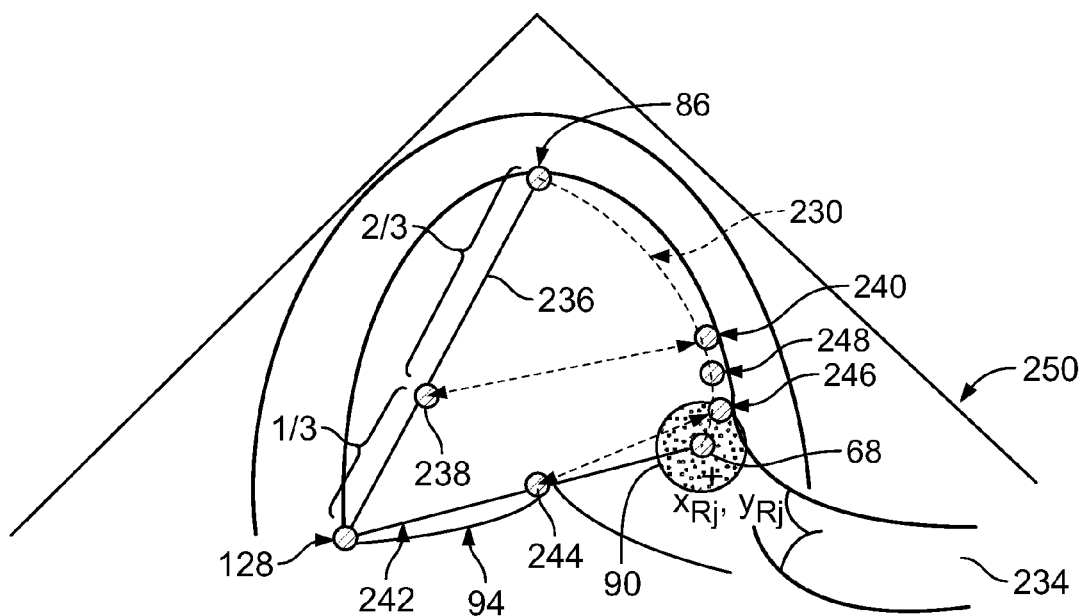
FIG. 9 illustrates a sector image showing the APLAX view and the adjustment of the right basal point in accordance with an embodiment of the present invention.

FIG. 8 illustrates a method for optimizing the user input right basal point 68 in the APLAX view 50. FIG. 9 illustrates a sector image 250 showing the APLAX view 50 and the adjustment of the right basal point 68. The following discussion of the adjustment of the right basal point 68 assumes that the apical point 64 and the left basal point 66 input by the user have been adjusted and/or optimized as discussed previously. However, the right basal point 68 may be adjusted based on one or both of the user input apical point 64 and left basal point 66. FIGS. 8 and 9 will be discussed together.

At 300, the processor module 36 defines the search area 90 around the right basal point 68. At 302 the processor module 36 defines a second plurality or grid of points $[(x_{R,j}, y_{R,j}), j=1, \ldots, N]$ around the right basal point 68 within the search area 90 as discussed previously in FIG. 5, such that the right basal point 68 is the center of gravity point $(x_{BR,0}, y_{BR,0})$. At 304 the processor module 36 calculates the average distance of all of the points in the grid from the center of gravity point.

At 306 the processor module determines border lines extending from the adjusted apical point 86 to each of the points in the second plurality of points $[(x_{R,j}, y_{R,j}), j=1, \ldots, N]$. A single border line 230 is shown as a dashed line extending from the adjusted apical point 86 to the right basal point 68. Again, the border line 230 is smoothly shaped, and in some embodiments may be elliptical in shape, and may be adjusted based on edge detection in the immediate area of the border line 230.

In the APLAX view 50, using the right leaflet of the mitral valve would include the outflow tract of the aorta 234, which is not desirable. Therefore, the right basal point 68 is not adjusted based on the right leaflet of the mitral valve.

At 308 the processor module 36 connects the adjusted left basal point 128 and the adjusted apical point 86 with line 236. At 310 the processor module 36 determines the location of a one-third distance point 238 that is approximately one-third of the distance between the adjusted apical point 86 and the adjusted left basal point 128, and is closer to the adjusted left basal point 128. It should be understood that other methods may be used to determine the one-third distance point 238. At 312 the processor module 36 determines points on the border lines 230 that are the closest points to the one-third distance point 238. On FIG. 9, a point 240 is illustrated on the border line 230 as the closest point to the one-third distance point 238.

At 314 the processor module 36 determines average x,y locations or half-way points 244 between the adjusted left basal point 128 and each of the plurality of grid points $[(x_{R,j}, y_{R,j}), j=1, \ldots, N]$. In this example, the illustrated grid point is the center of gravity point and is also the right basal point 68. For example, line 242 may be determined with the half-way point 244 indicated thereon.

At 316 the processor module 36 determines points on the border lines 230 that are closest to the half-way points 244. For example, point 246 illustrated on the border line 230 is closest to the half-way point 244. At 318, the processor module 36 determines average points that are an average between the two previously defined points on the border lines 230. For example, average point 248 is an average between the two previously defined points 240 and 246 on the border line 230. The average point 248 is the new point $(x'_{R,j}, y'_{R,j})$. Therefore, the previous plurality or grid of points is adjusted to generate a new plurality or cluster of points $[(x'_{R,j}, y'_{R,j}), j=1, \ldots, N]$ by moving each point in the grid to a respective average point 248. The adjusted points in the new plurality of points may no longer be uniformly distributed or contained within the search area 90.

When the new plurality or cluster of points $[(x'_{R,j}, y'_{R,j}) j=1, \ldots, N]$ has been determined, at 320 the processor module 36 determines a new or adjusted center of gravity point $(x'_{BR,0}, y'_{BR,0})$ associated with the cluster of points. At 322, the processor module 36 determines the average width of the cluster, defined as the average $d'_{average}$ of the distances $d'_j$ between each of the points $[(x'_{R,j}, y'_{R,j}) j=1, \ldots, N]$ and the center of gravity point $(x'_{BR,0}, y'_{BR,0})$.

The convergence is determined in the same manner as discussed previously in FIG. 5. At 324 the processor module 36 determines whether the new distance $d'_{average}$ is less than the previous distance $d_{average}$. If the new average distance is not less, at 330 the processor module 36 may indicate that the process is not converging, an error has occurred, or the previously determined center of gravity point should be identified as the adjusted or optimized right basal point. If the new average distance is less at 324, the process is converging and at 326 the processor module 36 determines whether the difference between the new and previous distances is below a predetermined limit. If the difference is not below a predetermined limit, the process returns to 306 to accomplish another iteration to determine a new center of gravity point and a new average distance.

Figure 10:
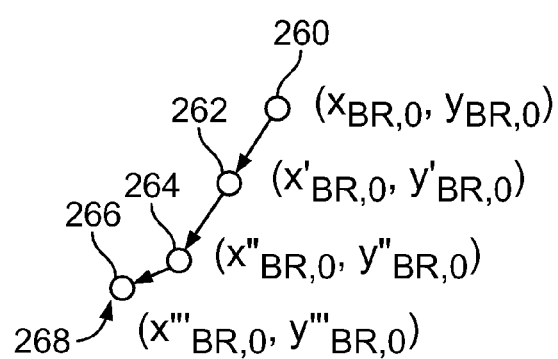
FIG. 10 illustrates a schematic representation of the convergence process of the successive centers of gravity for the right basal point in the APLAX view in accordance with an embodiment of the present invention.

FIG. 10 illustrates a schematic representation of the convergence process of the successive centers of gravity for the right basal point in the APLAX view. Point 260 is the user input right basal point 68, referred to as $(x_{BR,0}, y_{BR,0})$. Point 262 is the center of gravity point $(x'_{BR,0}, y'_{BR,0})$ after one iteration, point 264 indicates the center of gravity point $(x''_{BR},$ o, y"$_{BR,0}$) after two iterations, and point 266 indicates the center of gravity point (x'''$_{BR,0}$, y'''$_{BR,0}$) after three iterations.

Returning to 326 of FIG. 8, if the difference between consecutive center of gravity points is below the predetermined limit, at 328 the processor module 36 identifies the last determined center of gravity point as the adjusted or optimized right basal point. In the example of FIG. 10, the point 266 may also be referred to as the adjusted right basal point 268.

Once one or more of the user input points, the apical point 64, left basal point 66 and/or right basal point 68, have been adjusted or optimized, resulting in one or more of the adjusted apical point 86, adjusted left basal point 128 and adjusted right basal point 268, the processor module 36 may automatically determine the borders or walls of the left ventricle. For example, the processor module 36 may determine a smoothly shaped border line that passes through the adjusted apical point 86 (or apical point 64) and the adjusted left basal point 128 (or left basal point 66) and is shaped or fitted to best describe the endocardium 58 (or endocardium border). The processor module 36 may also determine another smoothly shaped border line that passes through the adjusted apical point 86 (or apical point 64) and the adjusted right basal point 268 (or right basal point 68) and is shaped or fitted to best describe the endocardium 58. In addition, the processor module 36 may display the adjusted apical point 86 and adjusted left and right basal points 128 and 268 on the display 38. In one embodiment, the user may accept or reject each of the adjusted points. In another embodiment, the user may manually adjust one or more of the adjusted apical point 86 and adjusted left and right basal points 128 and 268 (or the user may manually adjust one or more of the user input apical point 64 and/or left and right basal points 66 and 68) with the user interface 42, such as by using a mouse or other pointer to drag one of the points to a new location.

A technical effect of at least one embodiment is to automatically adjust the locations of one or more of the user input apical point and left and right basal points to optimal values. The adjustment for each of the points may be performed separately. The apical point and left and right basal points may each be adjusted based on a spatial relationship to at least one of the other user input or adjusted points. The apical point is adjusted based on an autocorrelation of points located in stationary and non-stationary regions above the user input apical point. The left basal point may be adjusted based on the left leaflet of the mitral valve and the adjusted or user input apical point. The right basal point may be adjusted based on the right leaflet of the mitral valve and the adjusted or user input apical point if the two or four chamber view is used. For the APLAX view, the right basal point may be adjusted based on a relative relationship of the positions of the adjusted or user input apical point and the adjusted or user input left basal point to the user input right basal point.

Figure 11:
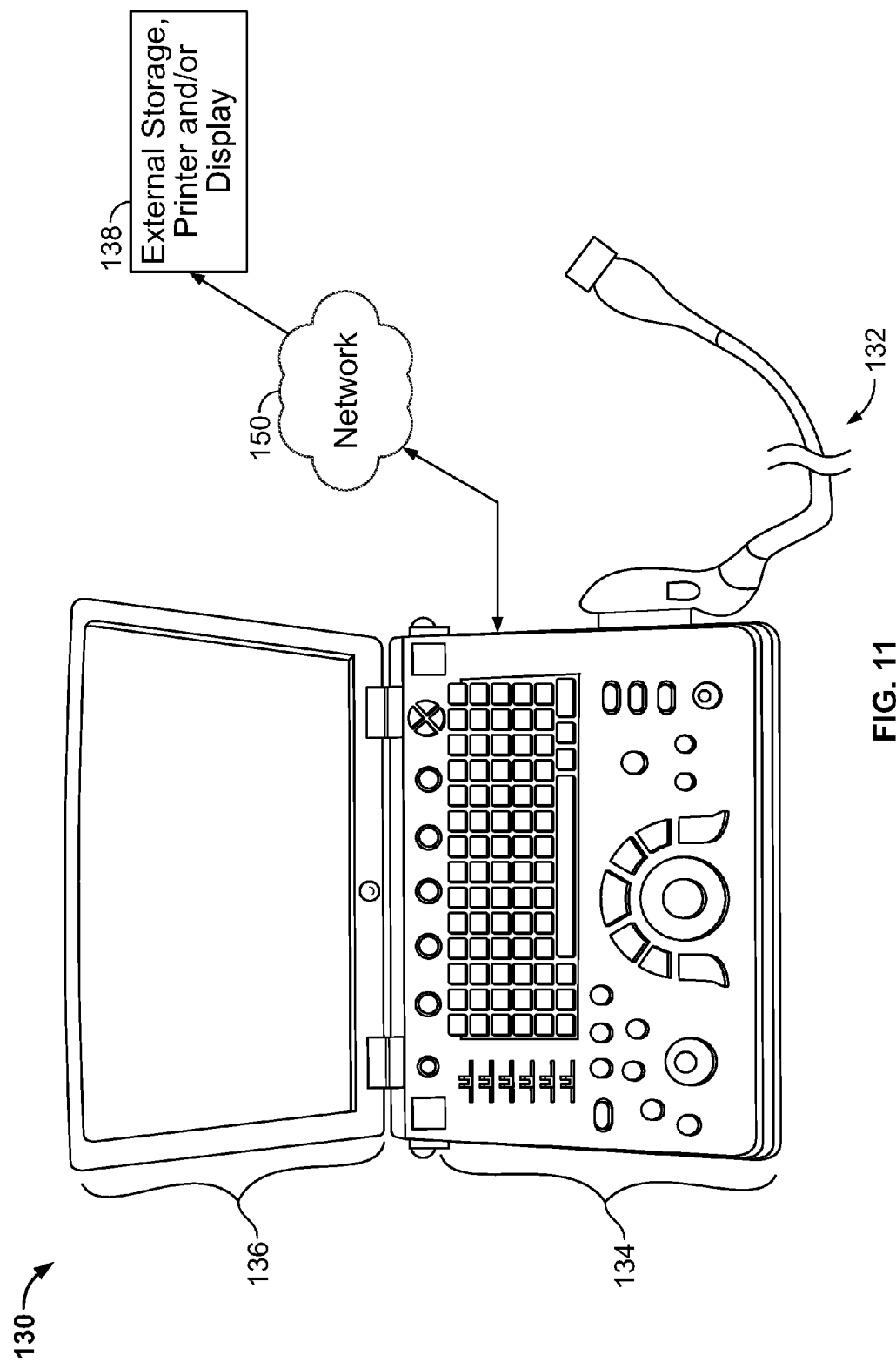
FIG. 11 illustrates a 3D-capable miniaturized ultrasound imaging system that may be configured to optimize the user input points in accordance with an embodiment of the present invention.

FIG. 11 illustrates a 3D-capable miniaturized ultrasound imaging system 130 having a transducer 132 that may be configured to optimize the user input points 64, 66 and 68 as previously discussed. For example, the transducer 132 may have a 2D array of transducer elements 24 as discussed previously with respect to the transducer 26 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 150 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136.

Figure 12:
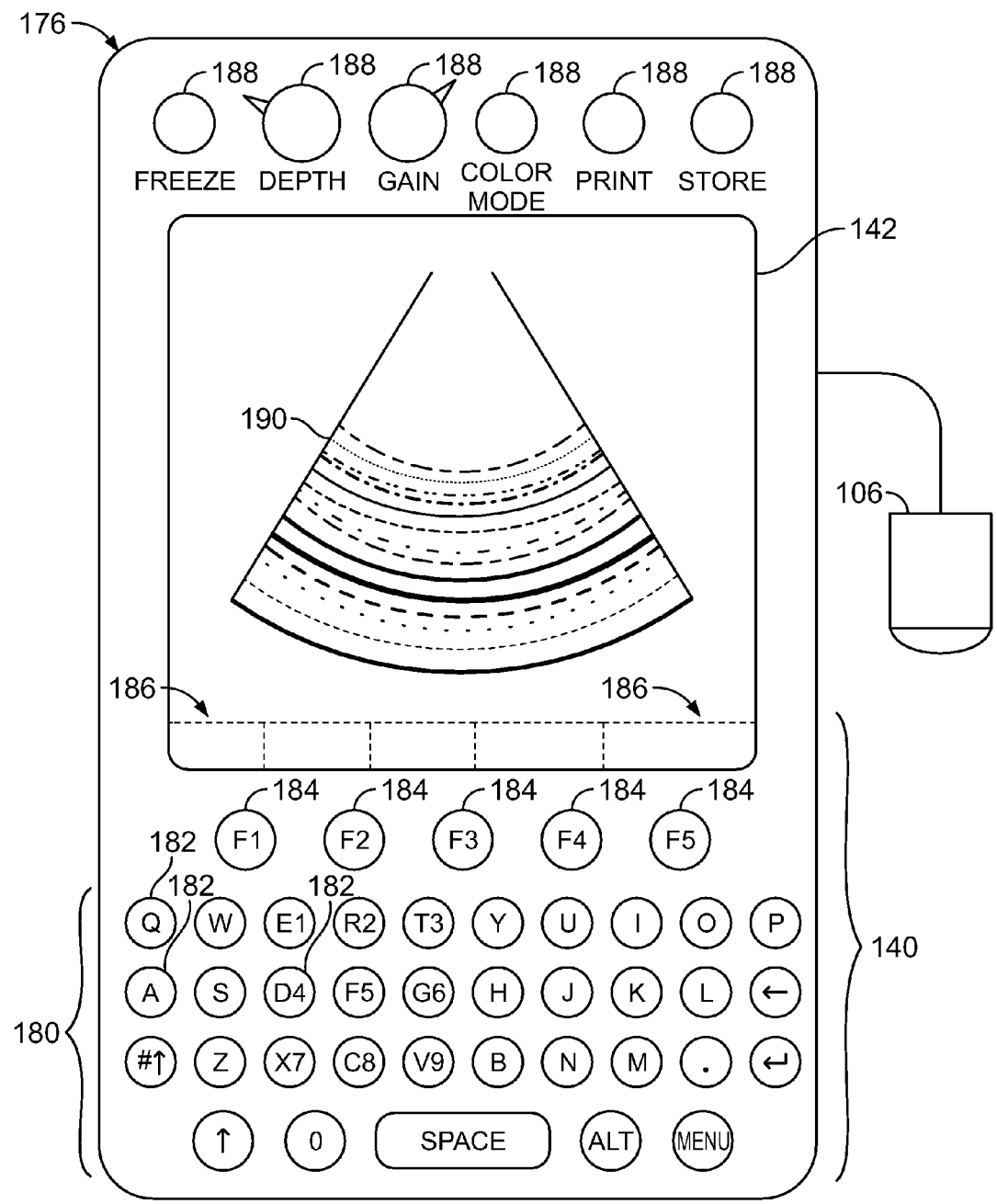
FIG. 12 illustrates a hand carried or pocket-sized ultrasound imaging system that may be configured to optimize the user input points in accordance with an embodiment of the present invention.

FIG. 12 illustrates a hand carried or pocket-sized ultrasound imaging system 176 that may be configured to optimize the user input points 64, 66 and 68. In the system 176, display 142 and user interface 140 form a single unit. By way of example, the ultrasound imaging system 176 may be a pocket-sized or hand-sized ultrasound system approximately 2 inches wide, approximately 4 inches in length, and approximately 0.5 inches in depth and weighs less than 3 ounces. The display 142 may be, for example, a 320×320 pixel color LCD display (on which a medical image 190 may be displayed). A typewriter-like keyboard 180 of buttons 182 may optionally be included in the user interface 140. It should be noted that the various embodiments may be implemented in connection with a pocket-sized ultrasound system 176 having different dimensions, weights, and power consumption.

Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 142. The system 176 may also have additional keys and/or controls 188 for special purpose functions, which may include, but are not limited to "freeze," "depth control," "gain control," "color-mode," "print," and "store."

Figure 13:
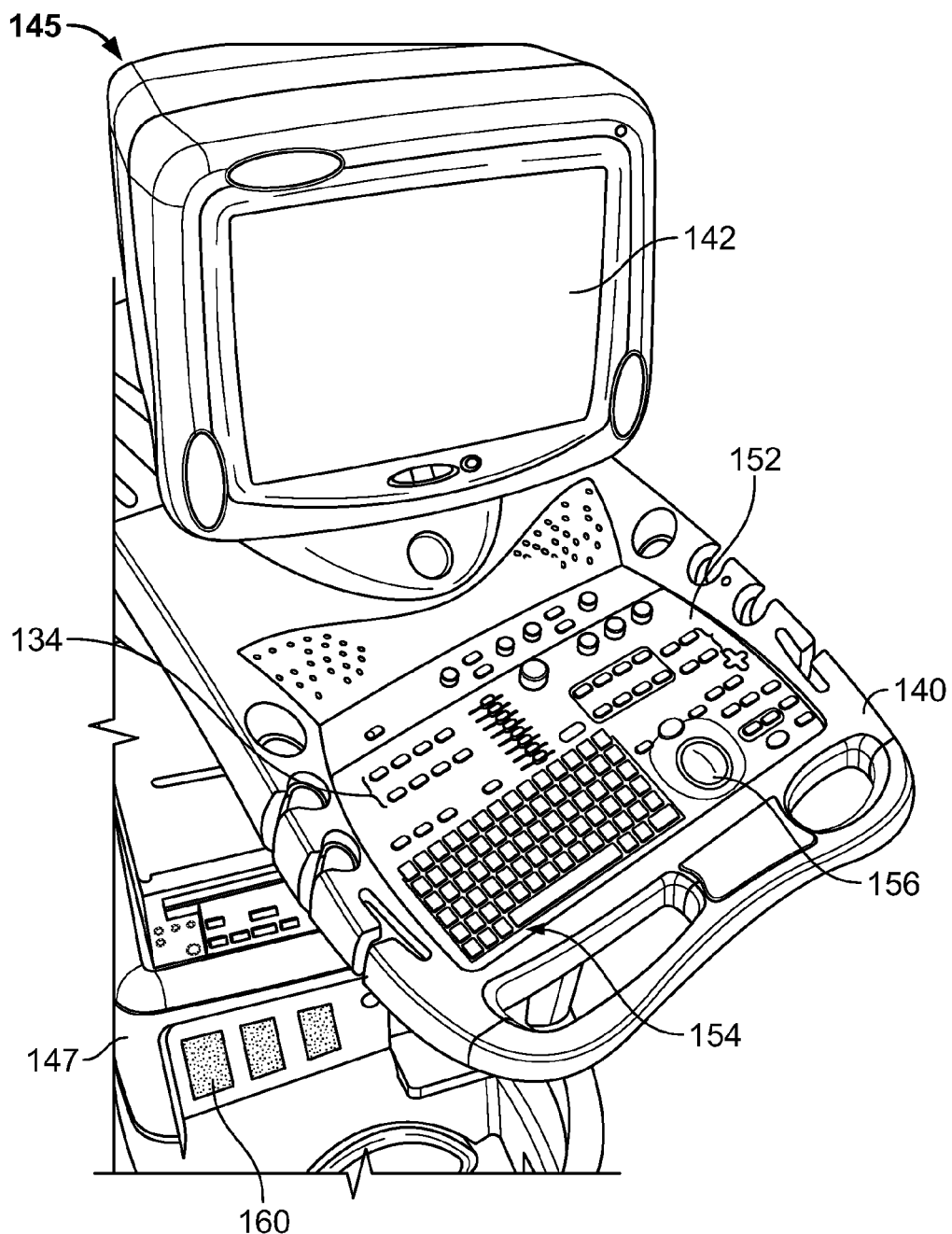
FIG. 13 illustrates a console-based ultrasound imaging system provided on a movable base that may be configured to optimize the user input points in accordance with an embodiment of the present invention.

FIG. 13 illustrates a console-based ultrasound imaging system 145 provided on a movable base 147 that may be configured to optimize the user input points 64, 66 and 68. The portable ultrasound imaging system 145 may also be referred to as a cart-based system. A display 142 and user interface 140 are provided and it should be understood that the display 142 may be separate or separable from the user interface 140. The user interface 140 may optionally be a touchscreen, allowing the operator to select options by touching displayed graphics, icons, and the like.

The user interface 140 also includes control buttons 152 that may be used to control the portable ultrasound imaging system 145 as desired or needed, and/or as typically provided. The user interface 140 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided. The system 145 has at least one probe port 160 for accepting probes.

Figure 14:
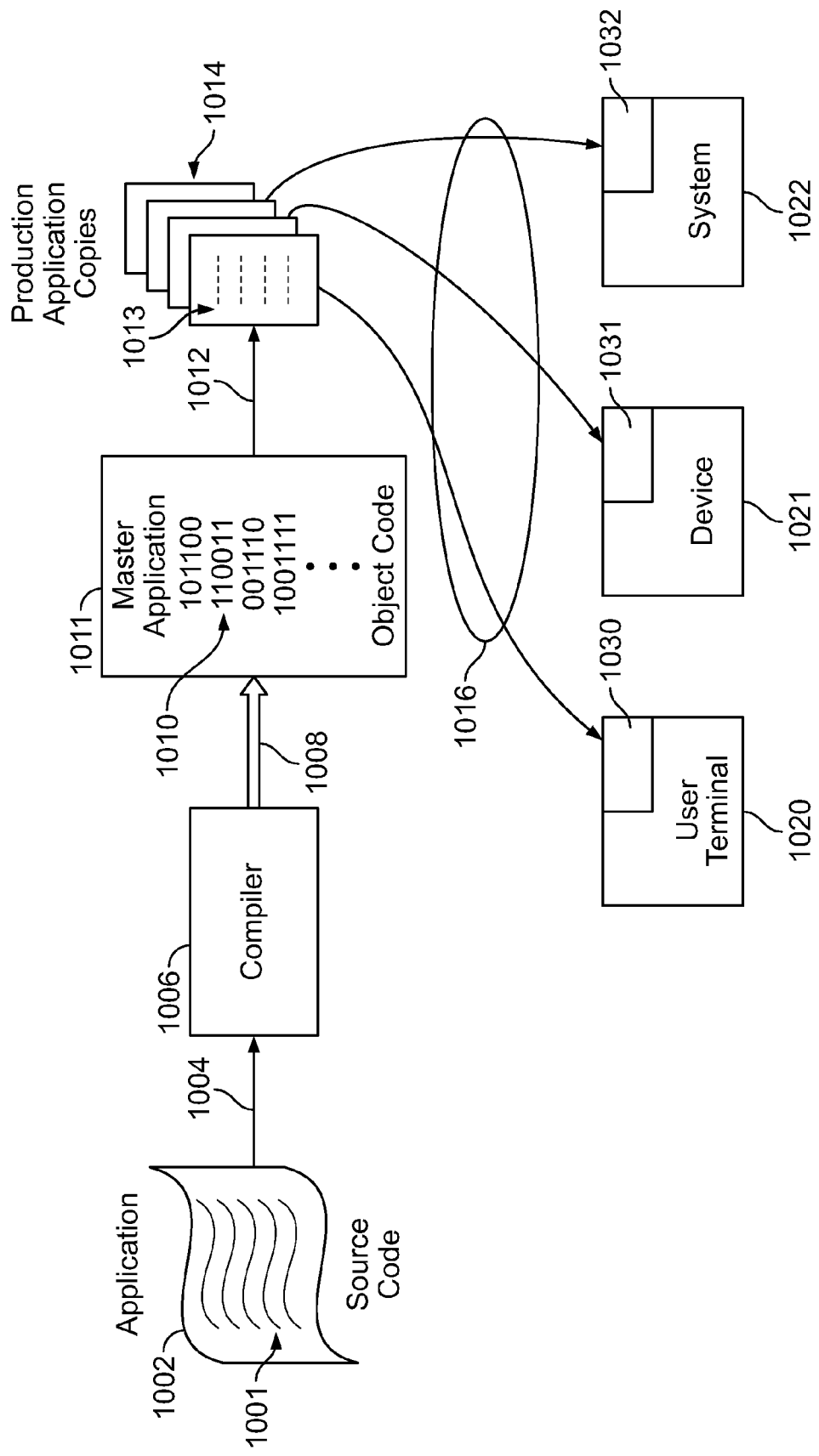
FIG. 14 illustrates a block diagram of exemplary manners in which embodiments of the present invention may be stored, distributed and installed on computer readable medium.

FIG. 14 illustrates a block diagram of exemplary manners in which embodiments of the present invention may be stored, distributed and installed on computer readable medium. In FIG. 14, the "application" represents one or more of the methods and process operations discussed above. For example, the application may represent the process carried out in connection with FIGS. 3-10 as discussed above.

As shown in FIG. 14, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 14, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

The operations noted in FIG. 14 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for optimizing user input points that identify points within an image of a left ventricle of a heart, the method comprising:
    identifying user input points on a single image, wherein the user input points comprise an apical point, a left basal point and a right basal point positioned proximate to an endocardium of a left ventricle using a processor;
    determining an adjusted apical point, using the left and right basal points, the adjusted apical point based on at least an autocorrelation of points located on a line defined by the left and right basal points, in the single image proximate to the apical point using the processor; and
    displaying, on a display device, the adjusted apical point on the single image.

2. The method of claim 1, wherein the points in the image are defined along a line extending between the apical point and an edge of the image proximate to the apical point, the line being configured to intersect a middle point between the left and right basal points, wherein the determining the adjusted apical point further comprises:
    temporally averaging values associated with the points over a period of time;
    autocorrelating the temporally averaged values; and
    determining an intersection point on the line based on a change in autocorrelation values determined for consecutive points along the line, the adjusted apical point being further determined based on the intersection point.

3. The method of claim 1, wherein the determining the adjusted apical point further comprises:
   determining an intersection point based on a change in autocorrelation values determined for consecutive points along a line extending between the apical point and an edge of the image proximate to the apical point, the line being configured to intersect a middle point between the left and right basal points; and
   identifying a width between the endocardium and an epicardium of the left ventricle based on the apical point and the left and right basal points, the adjusted apical point being further determined based on the intersection point and the width.

4. The method of claim 1, further comprising adjusting at least one of the left basal point and the right basal point based on a left leaflet and a right leaflet, respectively, of a mitral valve, wherein the left leaflet is located proximate to the left basal point and the right leaflet is located proximate to the right basal point.

5. The method of claim 1, further comprising:
   determining a left leaflet shape of a left leaflet of a mitral valve, the left leaflet being located proximate to the left basal point;
   extending border lines from the adjusted apical point through each of a plurality of points located proximate to the left basal point, the plurality of points having a center of gravity point corresponding to the left basal point, the border lines intersecting the left leaflet shape at intersection points, the plurality of points being adjusted based on the intersection points, the center of gravity point being adjusted based on the adjusted plurality of points; and
   adjusting the left basal point based on the adjusted center of gravity point.

6. The method of claim 1, wherein the image comprises one of a two chamber view and a four chamber view, the method further comprising:
   determining a right leaflet shape based on a best fit equation, the right leaflet shape forming a shape of a right leaflet of a mitral valve, the right leaflet being located proximate to the right basal point;
   extending border lines from the adjusted apical point through each of a plurality of points located proximate to the right basal point, the plurality of points having a center of gravity point corresponding to the right basal point, the border lines intersecting the right leaflet shape at intersection points, the plurality of points being adjusted based on the intersection points, the center of gravity point being adjusted based on the adjusted plurality of points; and
   adjusting the right basal point based on the adjusted center of gravity point.

7. The method of claim 1, further comprising:
   adjusting a plurality of points based on intersection points between a left leaflet shape based on a best fit equation and border lines extending from the adjusted apical point, each of the border lines extending through a point within the plurality of points, the left leaflet shape forming a shape of a left leaflet of the mitral valve, the plurality of points located proximate to the left basal point and having a center of gravity point corresponding to the left basal point;
   determining a first average distance between the plurality of points and the center of gravity point and a second average distance between an adjusted plurality of points and an adjusted center of gravity point, respectively, the adjusted center of gravity point being based on the adjusted plurality of points; and
   positioning the left basal point at the adjusted center of gravity point when the second average distance is less than the first average distance.

8. The method of claim 1, wherein the image comprises an apical long axis (APLAX) view, the method further comprising:
   defining a plurality of points located proximate to the right basal point, the plurality of points having a center of gravity point located at the right basal point; and
   adjusting the plurality of points based on a first point located between the left basal point and the adjusted apical point and a second point located between the left basal point and the right basal point, the right basal point being adjusted based on an adjusted center of gravity point associated with the adjusted plurality of points.

9. The method of claim 1, further comprising automatically defining on the image at least one of the endocardium and an epicardium of the left ventricle based on the adjusted apical point and the left and right basal points.

10. The method of claim 1, wherein determining an adjusted apical point using the left and right basal points further comprises:
    defining a first line between the left and right basal points;
    identifying a centerpoint in the first line; and
    defining a second line between the centerpoint and an edge of the image, the second line extending from the centerpoint, through the apical point, to the edge of the image, the adjusted apical point based on at least an autocorrelation of points located along the second line.

11. The method of claim 1, wherein determining an adjusted apical point using the left and right basal points further comprises:
    defining a centerpoint in a first line extending between the left and right basal points;
    defining a second line between the centerpoint and an edge of the image;
    defining a non-stationary point on the second line;
    defining a stationary point on the second line; and
    autocorrelating the non-stationary point with the stationary point to generate the adjusted apical point on the second line.

12. The method of claim 1, wherein determining an adjusted apical point using the left and right basal points further comprises:
    defining a line that extends through the apical point, a non-stationary point located on the left ventricle, and a stationary point located on a region outside the left ventricle; a and
    generating the adjusted apical point based on the line, the adjusted apical being located on the line between the non-stationary point and the stationary point.

* * * * *

UNITED STATES PATENT AND TRADEMARK OFFICE
CERTIFICATE OF CORRECTION

PATENT NO.        : 8,319,770 B2
APPLICATION NO.   : 12/172097
DATED             : November 27, 2012
INVENTOR(S)       : Friedman et al.

It is certified that error appears in the above-identified patent and that said Letters Patent is hereby corrected as shown below:

In Column 4, Line 15, delete "systoli," and insert -- systolic, --, therefor.

In Column 4, Line 16, delete "systoli." and insert -- systolic. --, therefor.

In Column 4, Line 18, delete "systoli." and insert -- systolic. --, therefor.

In Columns 6 & 7, Lines 67 & 1, delete "$d_{aver}$.age." and insert -- $d_{average}$. --, therefor.

In Column 14, Lines 57, in Claim 12, delete "a and" and insert -- and --, therefor.

Signed and Sealed this
Second Day of April, 2013

Teresa Stanek Rea
*Acting Director of the United States Patent and Trademark Office*